(12) United States Patent
Becker et al.

(10) Patent No.: US 6,180,229 B1
(45) Date of Patent: *Jan. 30, 2001

(54) HOT MELT PRESSURE SENSITIVE ADHESIVE COMPOSITION USEFUL FOR CONTACT COATING ON HEAT SENSITIVE SUBSTRATES

(75) Inventors: Hans-Ulrich Becker, Luneburg; Peter Remmers, Hamburg, both of (DE)

(73) Assignee: H. B. Fuller Licensing & Financing, Inc., St. Paul, MN (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/099,009

(22) Filed: Jun. 17, 1998

(51) Int. Cl.[7] .............................. C09J 7/02; C09J 153/00
(52) U.S. Cl. ........................ 428/355 BL; 428/355 RA; 428/198; 604/389; 604/386; 427/208.2; 427/208.4
(58) Field of Search ................ 428/355 RA, 355 BL, 428/198; 604/389, 386; 427/208.2, 208.4

(56) References Cited

U.S. PATENT DOCUMENTS

| | | |
|---|---|---|
| 4,136,699 | 1/1979 | Collins et al. . |
| 4,704,110 | 11/1987 | Raykovitz et al. . |
| 4,728,572 | * 3/1988 | Davis .................................... 428/355 |
| 5,019,071 | * 5/1991 | Bany et al. ........................... 604/389 |
| 5,300,057 | * 4/1994 | Miller et al. ......................... 604/390 |
| 5,714,254 | * 2/1998 | Jacob ............................ 428/355 BL |

FOREIGN PATENT DOCUMENTS

| | | |
|---|---|---|
| 0 525 251 A1 | 2/1993 | (EP) . |
| 0 745 368 A1 | 12/1996 | (EP) . |
| 0 745 432 A1 | 12/1996 | (EP) . |
| 0 745 433 A1 | 12/1996 | (EP) . |
| 0 794 202 A1 | 9/1997 | (EP) . |
| 0 885 942 | 12/1998 | (EP) . |
| 0 758 009 | 3/1999 | (EP) . |
| WO 96/25902 | 8/1996 | (WO) . |
| WO 99/13016 | 3/1999 | (WO) . |

* cited by examiner

Primary Examiner—Daniel Zirker
(74) Attorney, Agent, or Firm—Carolyn A. Fisher; Nancy N. Quan

(57) ABSTRACT

The invention is a disposable article comprising a discontinuous coating of a hot melt PSA permanently adhered to at least one substrate wherein the adhesive has a shear adhesion failure temperature of greater than about 79° C. (175° F.). Preferably, the adhesive is pattern coated directly onto a polyolefin film for use in a variety of articles including adhesive bandages, tape and feminine napkins.

21 Claims, 1 Drawing Sheet

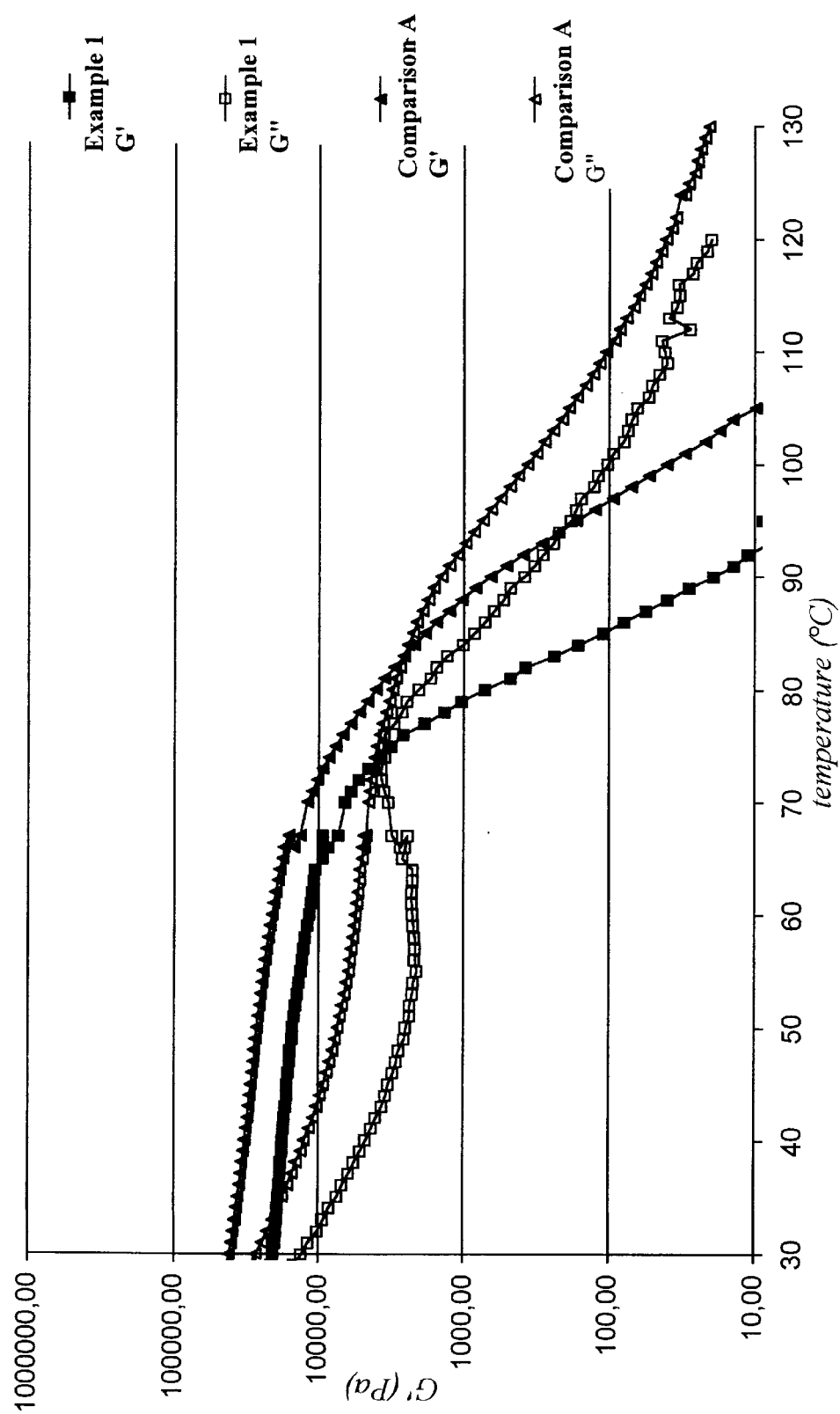
Figure A

HOT MELT PRESSURE SENSITIVE ADHESIVE COMPOSITION USEFUL FOR CONTACT COATING ON HEAT SENSITIVE SUBSTRATES

FIELD OF THE INVENTION

This invention relates to a hot melt pressure sensitive adhesive (HMPSA) compositions which is useful for coating onto heat sensitive substrates and articles constructed therefrom. In particular, the invention relates to a hot melt adhesive having certain rheological characteristics, indicative of a low softening point and a low molten viscosity in combination with high cohesive strength. These combinations of properties are particularly amenable to removable adhesive application wherein the adhesive is permanently adhered to a substrate and is subsequently "removably" adhered to a surface such as fabric or skin without adhesive transfer. Due to the low viscosity at low application temperatures, the adhesive composition is amenable to hot melt adhesive application methods wherein the coating device contacts the substrate being coated such as in the case of screen printing and engraved roll coating. The invention further relates to articles such as feminine napkins, tapes, and bandages wherein the novel HMPSA composition is coated onto a substrate.

BACKGROUND OF THE INVENTION

"Removable" or "releasable" HMPSA's are those in which the adhesive is permanently adhered to at least one substrate such as paper stock or a polyolefin film layer and then removably attached to a surface in order to secure an article for a period of time. Examples of articles utilizing removable HMPSA's include tapes, tags and labels and adhesive bandages. Feminine napkins, adult incontinent pads as well as some hospital pads and drapes also typically utilize removable HMPSA's commonly described as "garment attachment" or "positioning" adhesives. During manufacturing of such articles, the HMPSA is typically slot-coated directly onto a paper stock or polyolefin film substrate and then covered with a release liner. Alternatively, the adhesive may be transfer coated by first applying the adhesive to the release liner and subsequently contacting the adhesive to the substrate layer, sandwiching the hot melt PSA between the substrate and the release paper.

There are a multitude of patents pertaining to adhesive compositions for tapes, labels, adhesive bandages and the like. Alper et al., EP 525 251 A1, Collins et al., U.S. Pat. No. 4,136,699 and Raykovitz et al., U.S. Pat. No. 4,704,110 specifically relate to hot melt PSA positioning adhesives for feminine napkins. However, such patents are typically directed toward continuous slot-coating of the HMPSA.

EPO 794 202 A1 published Oct. 9, 1997 is directed to aliphatic petroleum-based resins, a method of controlling the softening point and molecular weight of such a resin, and HMPSAs containing such resins. The hot melt adhesive composition generally consists of S-I-S polymers containing 0 to 30 parts per weight of styrene.

In recent years, manufacturers have attempted to replace the continuous slot-coat method with various discontinuous methods, such as engraved roll coating and pattern coating methods, otherwise referred to as screen-printing. There are several advantages in utilizing these types of discontinuous coating techniques including aesthetic advantages due to the variety of designs as well as the ability to strategically place adhesive in precise locations. The primary advantage methods such as engraved roll coating and pattern coating offer is the ability to vastly reduce adhesive consumption since the surface area per mass of adhesive is greatly increased. However, this increase in surface area in combination with the adhesive being applied in small individual deposits rather than a continuous layer creates adhesive transfer concerns, particularly when the substrate coated is a polyolefin film. It is theorized that in order for the adhesive to have the proper balance of properties, the adhesion to the substrate must be greater than the cohesive strength of the hot melt PSA. Concurrently the cohesive strength of the adhesive must be greater than the adhesion to the surface to which the adhesive is removably attached. Adhesives that possess these qualities in a slot coat application typically exhibit adhesive transfer when engraved roll coated or pattern coated, particularly at high removal rates. Furthermore, since directly applying the adhesive to the substrate is preferred for these application methods to enhance adhesion, HMPSA's are needed that are low in viscosity at low application temperatures in combination with the proper balance of adhesion and cohesion. The applicants have found that certain novel hot melt pressure sensitive adhesive compositions meet these requirements.

SUMMARY OF THE INVENTION

The inventors have discovered that easily measured rheological properties of the adhesive can be used to predict the success of a removable HMPSA for discontinuously coating at low application temperatures. Although it is known from the Dahlquist criteria that PSAs exhibit a storage modulus of less than about $5 \times 10^6$ dynes/cm$^2$, the present inventors have discovered hot melt adhesive compositions that additionally exhibit a cross-over temperature of less than 85° C., preferably less than about 80° C. Since the crossover temperature is indicative of the melt point, the adhesives of the present invention melt at a significantly lower temperature. Additionally, the G' diminishes to below about 100 dynes/cm$^2$ at a temperature 10° C. cooler than low viscosity removable HMPSA compositions which are slot coated for use as positioning adhesive. Accordingly, the adhesive compositions of the present invention exhibit a G' of less than 100 dynes/cm$^2$ at a temperature of less than 95° C. and preferably at a temperature of about 90° C. or less. At about 10 dynes/cm$^2$ the adhesive composition is sufficiently molten such that the storage modulus (G') is difficult to measure. Further, the adhesive composition is also characterized as having a glass transition temperature (Tg) of about 0 or greater. Hence, the adhesive composition of the present invention have a relatively low molten viscosity at lower temperatures. Preferably, the Brookfield viscosity of the adhesive composition is less than about 5,000 at 125° C., and more preferably the viscosity is less than 5,000 cPs at 110° C. This combination of properties is particularly amenable to contact coating of heat sensitive materials such as pattern coating and engraved roller coating which entail applying the adhesive as a plurality of individual adhesive deposits. These rheological criteria are also believed to be amenable to other discontinuous coating methods, such as spiral spray and melt blown hot melt application methods.

In another embodiment, the present invention is a disposable article, such as a feminine napkin or a tape, comprising a HMPSA permanently adhered to at least one substrate wherein said adhesive has a crossover temperature of less than 85° C., preferably about 80° C. or less. The adhesive may be subsequently removably adhered to a surface such as fabric or skin. Preferably, the substrate is a polyolefin film layer.

The adhesive composition comprises at least one block copolymer having a styrene content of at least about 25% with respect to the total weight of the block copolymer, at least one aromatic tackifying resin, and at least one liquid diluent. Preferably, the adhesive comprises from about 10 wt-% to about 30 wt-% in the adhesive of a styrene-isoprene-styrene (SIS) or styrene-butadiene-styrene (SBS) block copolymer, from about 40 wt-% to about 65 wt-% of at least one aromatic-aliphatic tackifying resin; and from about 15 wt-% to about 35 wt-% of a plasticizer.

BRIEF DESCRIPTION OF THE DRAWINGS

FIG. A depicts a temperature sweep of Example 1 (squares), an adhesive composition of the present invention as well as Comparative Example A (diamonds). The storage modulus (G') is represented by the solid squares and diamonds, whereas the loss modulus (G") is represented by the unfilled squares and diamonds. Both compositions exhibit a storage plateau modulus in the range of about 20° C. to about 60° C. of less than about $5 \times 10^6$ dynes/cm$^2$, indicative of a pressure sensitive adhesive. The highest crossover temperature is the temperature at which G' and G" intersect. In the case of Comparative Example A, the crossover point occurs at about 85° C., whereas the adhesives of the present invention exhibit a crossover at a temperature of about 75° C.

DETAILED DESCRIPTION OF THE INVENTION

The present invention is a hot melt adhesive composition, a method of using such adhesive particularly for discontinuous contact coating and articles comprising a removable HMPSA permanently adhered to at least one substrate, and articles. The crossover temperature is indicative of the onset of melting. The adhesive exhibits a crossover temperature of less than 85° C. and more preferably about 80° C. or less in combination with the storage modulus ranging from about $5 \times 10^4$ dynes/cm$^2$ to about $5 \times 10^6$ dynes/cm$^2$ and preferably from about $1 \times 10^5$ dynes/cm$^2$ to about $5 \times 10^6$ dynes/cm$^2$. For the adhesives of the present invention, the crossover temperature is as low as possible without sacrificing the storage modulus plateau below the targeted range. Additionally, the G' diminishes to below about 100 dynes/cm$^2$ at a temperature 10° C. cooler than low viscosity removable PSA compositions which are slot coated for use as positioning adhesive. Accordingly, the adhesive compositions of the present invention exhibit a G' of less than 100 dynes/cm$^2$ at a temperature of less than 95° C. and preferably at a temperature of about 90° C. or less. Further, the adhesive composition of the present invention typically has a glass transition temperature (Tg) of about 0° C. or greater. The applicants have found that these easily measured and easily discernible measurements of a hot melt adhesive composition are predictive as to whether a discontinuous coating of the adhesive will transfer upon removal.

The removable pressure sensitive adhesive comprises at least one thermoplastic polymer present in an amount ranging from about 10 wt-% to about 50 wt-%, preferably from about 10 wt-% to about 40 wt-%, more preferably from about 10 wt-% to about 30 wt-%, and most preferably from about 10 wt-% to about 20 wt-%. At too high of concentrations, typically in excess of about 25 wt-%, the adhesive composition tends to exhibit too high of a viscosity to be applied at low application temperatures, whereas at polymer concentrations less than about 10 wt-%, the adhesive lacks sufficient cohesive strength. For polymers having a relatively high molecular weight, wherein the melt index is less than about 10 g/10 minute, lower concentrations of polymer generally provide sufficient cohesive strength, whereas higher polymer concentration are needed when lower molecular weight polymers are employed. Preferably, the polymer is an A-B-A block copolymer; wherein said A block is polystyrene and said B block is isoprene, butadiene, ethylene-butylene, ethylene-propylene or mixtures thereof. Preferably, the block copolymer has a styrene content greater than about 25% styrene, since the styrene content has an increasing effect on the cohesive strength and reduces transfer tendencies. Lower styrene content block copolymers are also useful, particularly when blended with at least one high styrene block copolymer, greater than about 25% styrene, or when used in combination with a high softening point endblock reinforcing tackifying resins. The block copolymer may be linear or preferably radial in structure to minimize viscosity at application temperature.

Particularly for engraved roller coating applications, the adhesive composition comprises a block copolymer having an unsaturated midblock such as styrene-isoprene-styrene (SIS) or styrene-butadiene-styrene (SBS) block copolymer, the SIS being more preferred. Preferably the styrene content of the block copolymer is at least 25%, preferably about 30% or greater, and more preferably about 40% or greater. The block copolymer preferably has a melt index (MI, Condition G) ranging from about 10 g/10 min to about 60 g/10 min and more preferably from about 20 g/10 min. to about 40 g/10 min. The block copolymers having a styrene content of less than about 25% or an MI higher than 60 disadvantageously lack sufficient cohesive strength causing adhesive transfer when employed alone. However, such polymer may be employed if blended with another polymer such that the melt index and/or styrene content of the blend is within the desired range.

Other polymers that may be suitable alone as a base polymer or in combination with the block copolymer for HMPSA's include amorphous polyolefins commercially available from Huls and Rexene under the tradenames Vestoplast® and Rextac® and metallocene catalyzed polyolefins commercially available from Exxon under the tradename Exact®, and from Dow/Dupont under the tradenames Affinity™ and Engage™. The metallocene catalysis results in homogeneous linear or substantially linear interpolymers of ethylene with at least one alpha-olefin wherein the polydispersity is less than about 2.5. Other useful polymers for formulating HMPSA's include polyesters, particularly Eastman Chemical's water dispersible copolyesters such as AQ 1045 and AQ 1350 as well as hot melt moisture cures and polyurethanes.

The adhesive of the invention comprises a tackifying resin. Tackifying resins range from being a liquid at 37° C. to having a ring and ball softening point of about 135° C. Solid tackifying resins are present in amounts up to about 65% by weight. However, if liquid tackifiers are employed, the tackifier concentration may exceed 65% by weight. Preferably, the tackifying resin is present in an amount ranging from about 20% to about 65% by weight, more preferably from about 40% to 65% by weight. At too high of a resin concentration, the adhesive is too stiff exhibiting zippery or slip-stick types peel properties, whereas at too low of a resin concentration, poor processing characteristics such as angle-hairs occur. Tackifying resins useful in the present invention comprise resins derived from renewable resources such as rosin derivatives including wood rosin, tall oil, gum rosin; rosin esters, natural and synthetic terpenes, and derivatives of such. Aliphatic, aromatic or mixed aliphatic-aromatic petroleum based tackifiers are also useful in the adhesive of this invention. Representative examples of useful hydrocarbon resins includes alpha-methyl styrene resins, branched and unbranched $C_5$ resins, $C_9$ resins, $C_{10}$ resins, as well as styrenic and hydrogenated modifications of such.

By employing certain tackifying resins, the slope of the storage modulus (G') at temperatures greater than the storage modulus plateau can be shifted to lower temperatures without sacrificing the storage modulus plateau. To acquire this property, preferably the tackifying resins comprises a mixture of aliphatic and aromatic constituents. The aromatic content is preferably at least about 20 wt-% with respect to the weight of the resin. Further, in embodiments wherein mixtures of tackifying resins are employed at least 40% preferably 50%, and more preferably 70% or higher of the total resin concentration is an aromatic resin having at least about 20% aromaticity, Representative examples include MBG-275, a 100° C. softening point hydrogenated C9 resin available from Hercules and Escorez 5600, an aromatically modified dicyclopentadiene resin available from Exxon (Houston, Tex.). The aromaticity allows such resin to soften the styrenic endblock which consequently reduces the melting point of the adhesive and flattens the viscosity curve.

Alternatively, a predominantly aliphatic tackifying resin may be combined with a tackifying resins that is aromatic in character. Commercially available predominantly aliphatic tackifying resins suitable for use in the present invention include Arkon P 90, Arkon P 125, Arkon P 140, fully saturated alicyclic hydrocarbon resins from the Arakawa Chemicals Industries Ltd.; ESCOREZ 5300, ESCOREZ 5320, ESCOREZ 5340 and ESCOREZ 5380, dicyclopentadiene resins from Exxon Chemical Company; as well as less hydrogenated versions such as the ESCOREZ 5400 series and Hercules REGALITE R-stype resins.

Useful aromatic resins are available from Hercules Inc. under the tradename Kristalex® and typically have a softening point greater than about 100° C., more preferably the softening point ranges from about 120° C. to about 160° C. Polyphenyleneoxide (PPO) is another useful endblock reinforcing resin. Samples of experimental products containing PPO preblended with either a tackifier or a block copolymer are currently available from Arizona and Shell Chemical.

A minimum amount of fluid ingredient is necessary to the present invention. Such fluid ingredient may be provided as a plasticizer, a liquid resin, a liquid elastomer or any other material which flows at ambient temperatures. A plasticizer is useful broadly and can be defined as a typically organic composition that can be added to thermoplastics, rubbers and other resins to improve extrudability, flexibility, workability, or stretchability. Preferably the plasticizing agent is a liquid at ambient temperature, such as hydrocarbon oils, polybutene, liquid tackifying resins, liquid elastomers, and is present in amounts up to about 50 wt-%. More preferable, the plasticizer is an oil present in amount ranging from about 10% by weight to about 50% by weight and most preferably from about 15% by weight to about 35% by weight. Such oils are primarily hydrocarbon oils, low in aromatic content and are paraffinic or naphthenic in character. The oils are preferably low in volatility, transparent and have as little color and odor as possible. The plasticizers useful in this invention also includes the use of olefin oligomers, low molecular weight polymers, vegetable oils and their derivatives and similar plasticizing liquids.

As is known in the art, various other components can be added to modify the tack, color, odor, etc., of a hot melt adhesive. In particular, in applicants have found that a small concentration of wax can be used to increase the cohesive strength and/or reduce the peel. It is generally preferred that the other components or ingredients should be relatively inert and have negligible effects upon the properties contributed by the block copolymer, tackifying agent and plasticizer. Antioxidants and other stabilizing ingredients are also typically added to protect the adhesive from various heat and light induced degradation.

The present invention is particularly useful for engraved roll coating and pattern coating. Pattern coating involves extruding a hot melt adhesive through a rotating screen which then in turn deposits the adhesive directly onto the substrate to be coated. Alternatively, the screen may deposit the adhesive first onto release paper and then transfer coat the adhesive onto the intended substrate. The screens typically used in this process range from about 15 mesh to about 195 mesh, preferably from about 30 to 60 mesh, more preferable from about 30 to 40 mesh. The 30 to 60 mesh screen results in individual hot melt adhesive deposits ranging in mass from as little as about $5 \times 10^{-5}$ grams per adhesive deposit to about 0.05 grams per adhesive deposit.

In the case of an engraved roller applications, the adhesive is provided in a molten form in a reservoir. A roller which has been engraved with depressions is positioned such that as the roller revolves, a portion of the roller contacts the molten adhesive. Excess molten adhesive which is not present within the depressions is typically scraped off the roller. The roller is then subsequently contacted to a substrate, depositing the adhesive which was within the engraved depressions onto the substrate. The temperature of the roller may be controlled by a heating and/or cooling means. In any event the roller typically reaches the temperature of the molten adhesive ranging from about 90° C. to about 180° C. For heat sensitive substrate such as low gauge polyolefin films preferably the temperature of the roller does not exceed about 160° C., more preferably the roller is maintained at a temperature of about 140° C. or less and more preferably at a temperature ranging from about 90° C. to about 125° C.

After coating by either of these methods, the number of individual hot melt adhesive deposits per area of substrate ranges from as little as 1 per square inch to as many as about 600 per square inch. The total mass of adhesive per area ranges from as little as about 5 $g/m^2$ to about 50 $g/m^2$. Amounts greater than about 50 $g/m^2$ exceed the coating weight currently used for most slot coat applications. However, higher amounts may be useful for some applications requiring very aggressive adhesion.

Preferably, the adhesive is coated directly onto the substrate. When this technique is employed in the case of pattern coating, the individual adhesive deposits are pyramidal in shape with a substantially square shaped base adhered to the substrate. All four faces of the pyramidal shaped adhesive deposit can then removably adhere to another surface, particularly when the surface being bonded is deformable to some extent such as skin or fabric. Transfer coating may also be suitable. However, transfer coating results in the tips of the pyramids being adhered to the substrate with the base of the pyramids facing outward. This configuration is less desirable, particularly since most of the heat has dissipated by the time the adhesive is transferred onto the substrate.

In the case of engraved roll coating, the shape of the adhesive deposit corresponds to the engraving or etched depressions on the coating roller surface. Hence, the shape of the adhesive deposits vary from striped patterns, company logos and lettering to dots and squares in various arrangements.

The present invention is not limited to any particular shape of individual adhesive deposits. Since screens are typically manufactured having square shaped voids in the case of pattern coating, the resulting adhesive deposit is a four-sided pyramid having a square base. However, triangular, circular, elliptical, etc. voids are also contemplated. Hemispherical adhesive deposits are anticipated to be preferred.

In order for the hot melt adhesive to be suitable for direct coating onto heat sensitive polyolefin films, the HMPSA must have a low viscosity at a temperature less than about 300° F., more preferably less than about 275° F., most preferably less than about 250° F. The viscosity of the HMPSA at the application temperature is typically less than about 15,000 cps at 275° F., preferably less than about 5,000 cps. It is desired that the molten viscosity be as low as possible at as low of a temperature as possible without reducing the storage modulus below the targeted range. Hence, more preferably the viscosity of the adhesives is less than about 2,000 cPs, even more preferably less than about 1,000 cPs, and most preferably about 500 cPs. Adhesives having a Brookfield viscosity of greater than about 15,000 cps at the application temperature are too viscous to be coated, particularly when the adhesive deposit is less than about 40 mesh. At temperatures above 275° F., polyolefin films typically exhibit heat induced distortion.

As previously mentioned, discontinuous coating methods such as spray, engraved roller and pattern coating are particularly preferred over slot coating due to the ability to greatly increase the surface area per mass of adhesive. This increase in surface area provides sufficient adhesion, comparable to adhesion levels of slot-coat applications at far less adhesive consumption levels. Pattern coating offers other advantages such as the ability to strategically place small amounts of adhesive in precise locations. This aspect is particularly important for applying water sensitive adhesives to disposable absorbent articles such as disposable diapers and feminine napkins to improve fluid acquisition or to adhere super absorbent polymers. Additionally, the dimensional aspect of the individual adhesive deposits is surmised to improve shear properties. Furthermore, since engraved roll coating and pattern coating of hot melt adhesive is similar to screen-printing clothing, these types of coating methods are amenable to creating aesthetic advantages since a variety of designs such as trademarks and company logo's are possible. However, these advantages can only be realized for removable HMPSA if the adhesive remains permanently adhered to the substrate during usage and does not transfer onto the surface from which it is intended to be removable. Although engraved roll coating and pattern coating is exemplified, the adhesive composition of the present invention is expected to be useful for any coating method of a removable HMPSA, particularly discontinuous coating methods, since the inherent problem is essentially the same.

The HMPSA adhesive useful in the present invention is not necessarily limited to any particular class of adhesives. However, the adhesive must possess a sufficiently low viscosity at the application temperature to insure ease in processing. This aspect is of particular importance for direct coating of heat sensitive polyolefin films. Most preferable, the adhesive does not exhibit any plasticizer staining tendencies. If the plasticizer concentration exceeds the binding power of the polymer, the plasticizer tends to migrate to the surface under pressure and elevated temperature. This plasticizer migration causes adhesive transfer and residual transfer problems.

The adhesive composition is particularly useful for a variety of "removable" or "releasable" adhesive applications. For such embodiments, the novel HMPSA composition permanently adhered to at least one substrate such as paper stock, film, foil, or laminate and then removably attached to a surface in order to secure an article for a period of time. Examples of articles utilizing removable HMPSA's include tapes, tags, labels and adhesive bandages. Feminine napkins, adult incontinent pads as well as some hospital pads and drapes also typically utilize removable HMPSA's commonly described as "garment attachment" or "positioning" adhesives for securing the article to fabric.

In the case of disposable absorbent articles such as feminine napkins, the positioning adhesive is typically coated to a body fluid impermeable substrate such as a film. An absorbent material is directly or indirectly attached to the body fluid impermeable substrate on the opposite side as the positioning adhesive. The absorbent is also typically covered or surrounded by a body fluid permeable cover. Alternatively, the positioning adhesive may serve a dual function and also serve as the body fluid impermeable barrier.

During manufacturing of such articles, the HMPSA is typically slot-coated directly onto a paper stock or polyolefin film substrate and then covered with a release liner. Alternatively, the adhesive may be transfer coated by first applying the adhesive to the release liner and subsequently contacting the adhesive to the substrate layer, sandwiching the hot melt PSA between the substrate and the release paper. Advantageously, the adhesive compositions of the present invention are low in viscosity at low application temperatures and thus are well-suited for methods in which the hot melt adhesive applicator is contacted to a heat sensitive substrate. These properties are particularly amenable to engraved roll coating and pattern coating. The adhesive may be coated at relatively low temperatures ranging from about 90° C. to about 140° C. and preferably from about 90° C. to about 125° C.

The present invention can also be exemplified by the following non-limiting examples. Examples 1–3 were made in a sigma-blade mixer using known hot melt adhesive blending techniques. In addition to the physical properties measured for each of the compositions, the adhesives were engraved roll coated onto a polyolefin film at coat weights ranging from about 15 to about 30 g/m2. The depressions of the engraved roller coated ranged from 40–500 microns. The peel adhesion of the engraved roll coated samples were also tested and found not to transfer adhesive onto the fabric.

Test Methods

1. The Brookfield Viscosity was determined with Brookfield models DVH, DV-II or DV-III. An appropriate spindle size and hot melt adhesive sample size was selected in accordance with the viscometer manufacturers instructions. The adhesive sample was melted in the thermocel at the temperature at which the viscosity was to be measured. The spindle was lowered into the melted adhesive sample. The motor was turned on at the lowest speed and the corresponding torque reading displayed. The speed was increased until the torque reading stabilized and the viscosity measurement recorded after 30 minutes.

2. The Ring and Ball Softening Point was determined with a Herzog MC 753 instrument. The rings were preheated to the melt temperature and then placed on release paper. The melted adhesive sample was then poured into the rings without inclusion of air bubbles. After cooling, excess adhesive was removed from the rings and two samples placed in the holder of the apparatus with a steel balls on top of each sample. The samples were lowered into a glycerin filled beaker positioned on a heating plate. The samples were lowered into the glycerin and heated at a rated of 5° C. per minute. The average temperature at which the balls have fallen is recorded, the difference being not more than 1° C.

3. The Needle Penetration was measured in accordance with DIN 51579 with a load of 100 g and a rate of 5 seconds.

4. The T-Peels to a Textile Material was determined by first preparing hot melt coated adhesive films on Mylar or polyolefin film using a suitable coating device at an appropriate application temperature. During preparation of the adhesive film, the adhesive surface is covered with release paper to facilitate handling. The coat weight is checked targeting the indicated coat weight or 40 g/m²+/−3 g/m² where not indicated otherwise. The adhesive coated films are cut into 25 mm wide strips which are 170 mm in length in the machine direction. The release paper was removed and the adhesive surface of one 1 of the strips placed onto the textile* test fabric. The sample is placed on a mechanical roll-down device (2250 g at 120 inches/min), and the roller allowed two passes over the sample, one forward and one back. The strips are cut in the middle to obtain two samples. The strip is placed into the mobile jaw and the fabric is placed in the stationary jaw. The procedure is repeated three times (six samples), recording the average T-peel value and noting any legging or transfer. The T-peel values are reported in grams per linear inch. It is preferred to have T-peels in the 100–500 g range, most preferred in the 200–500 g range without adhesive transfer.

*Test fabrics available from TestFabrics (style 460.30 cotton interlock knit prewashed at 95° C., style 322 nylon tricot 6 prewashed at 40° C., and satin reference 010682 prewashed at 40° C.) Prewashing is done without detergent.

5. For the Time, Temperature Pressure test the same procedure as the "Initial Peel" was followed with the exception that after the adhesive coated surface is contacted with the test fabric, it is conditioned in a 38° C. oven for 15 hours under a pressure of 0.8 g/m² and then conditioned at ambient temperature prior to peeling.

6. The Rheological Measurements including the Loss Modulus, G", the Storage modulus, G', at 25° C. and the Tg were determined using a Bohlin Controlled Stress Rheometer with a target strain of 0.01. The parallel plates used had a 20 mm diameter and a 1.5 mm gap. The instrument was set to a frequency of 1 hertz (not 10 rads/sec) and temperature sweep was performed for the desired temperature range at a temperature increase of 0.2° C. per 6 seconds or other parameters in accordance with ASTM D4440-93.

| Ingredient | Tradename | Parts |
| --- | --- | --- |
| 44% styrene, 100% triblock SIS Block Copolymer | Vector 4411 (Dexco) | 14 |
| Tackifying Resin | MBG-275 (Hercules) | 40.0 |
| Antioxidant | Irganox 1010 (Ciba Geigy) | 0.3 |
|  | Irganox PS 800 | 0.3 |
| Plasticizing Oil | Shell Oil N 4142 FU (Shell) | 31.4 |
| Tackifying Resin | Regalite R-101 (Arizona) | 12.0 |
| Ring & Ball Softening Point | | 77° C. |
| Needle Penetration at 25° C. | | 87¹/₁₀ mm |
| Viscosity at 125° C. | | 1145 mPa · s |
| Glass Transition Temperature (Tg) | | 7° C. |

| Ingredient | Tradename | Parts |
| --- | --- | --- |
| 44% styrene, 100% triblock SIS Block Copolymer | Vector 4411 (Dexco) | 14 |
| Tackifying Resin | MBG-275 (Hercules) | 38.0 |
| Antioxidant | Irganox 1010 (Ciba Geigy) | 0.3 |
|  | Irganox PS 800 | 0.3 |
| Plasticizing Oil | Shell Oil N 4142 FU (Shell) | 31.4 |
| Tackifying Resin | Regalite R-101 (Arizona) | 12.0 |
| 110° C. melt point Fischer-Tropsch wax | Vestovax H2 | 2.0 |
| Ring & Ball Softening Point | | 79° C. |
| Needle Penetration at 25° | | 64¹/₁₀ mm |
| Viscosity at 125° C. | | 853 mPa · s |
| Glass Transition Temperature (Tg) | | −1.1° C. |
| Initial Peel Strength (N/25 mm) | | |
| Cotton | | 2.3 ± 0.1 |
| Nylon | | 3.1 ± 0.3 |
| Polyester | | 2.4 ± 0.2 |
| Time, Temperature, Pressure | | |
| Cotton | | 3.7 ± 0.1 |
| Nylon | | 5.7 ± 0.3 |
| Polyester | | 5.6 ± 0.3 |

| Ingredient | Tradename | Parts |
| --- | --- | --- |
| 44% styrene, 100% triblock SBS Block Copolymer | Vector 4461 (Dexco) | 14 |
| Tackifying Resin | MBG-275 (Hercules) | 38.0 |
| Antioxidant | Irganox 1010 (Ciba Geigy) | 0.3 |
|  | Irganox PS 800 | 0.3 |
| Plasticizing Oil | Shell Oil N 4142 FU (Shell) | 31.4 |
| Tackifying Resin | Regalite R-101 (Arizona) | 12.0 |
| 110° Fischer Tropsch Wax | Vestovax H2 | 2.0 |
| Ring & Ball Softening Point | | 73° C. |
| Needle Penetration at 25° | | 62¹/₁₀ mm |
| Viscosity at 125° C. | | 1318 mPa · s |
| Glass Transition Temperature (Tg) | | −3.3° C. |
| Initial Peel Strength (N/25 mm) | | |
| Cotton | | 2.1 ± 0.1 |
| Nylon | | 2.4 ± 0.2 |
| Polyester | | 2.2 ± 0.1 |
| Time, Temperature, Pressure | | |
| Cotton | | 4.1 ± 0.5 |
| Nylon | | 6.2 ± 0.4 |
| Polyester | | 5.8 ± 0.3 |

What is claimed is:

1. An article comprising a hot melt pressure sensitive adhesive permanently adhered to at least one substrate wherein said adhesive has a crossover temperature of less than about 80° C. and a Brookfield viscosity of less than 5,000 at 125° C.

2. The article of claim 1 wherein the adhesive has a G' of less than about 100 dynes/cm² at a temperature of less than about 90° C.

3. The article of claim 1 wherein the adhesive has a Tg of about 0 or greater.

4. The article of claim 1 wherein said substrate is a polyolefin film.

5. The article of claim 1 wherein said article is a feminine napkin.

6. The article of claim 1 wherein said article is a tape.

7. The article of claim 1 wherein said article removably adheres to a second substrate without transfer.

8. The article of claim 1 wherein said adhesive is present as a plurality of individual adhesive deposits.

9. The article of claim 1 wherein said adhesive comprises:
   a) from about 10% by weight to about 30% by weight of at least one A-B-A block copolymer;
   b) from about 20% by weight to about 65% by weight of a tackifying resin; and
   c) from about 15% to about 35% by weight of plasticizing oil.

10. The article of claim 9 wherein said adhesive has a G' of less than about 100 dynes/cm$^2$ at a temperature of less than about 90° C.

11. The article of claim 9 wherein said adhesive has a Tg of about 0 or greater.

12. The article of claim 9 wherein said block copolymer of the adhesive has a styrene content greater than about 25%.

13. The article of claim 9 wherein the block copolymer of the adhesive is styrene-isoprene-styrene, styrene-butadiene styrene, or mixtures thereof.

14. The article of claim 9 wherein said adhesive has a Brookfield viscosity of less than about 5,000 at about 110° C.

15. The article of claim 9 wherein the tackifying resin of the adhesive is a mixed aliphatic-aromatic tackifying resin.

16. The article of claim 15 wherein the tackifying resin of the adhesive has an aromatic content of at least about 20 wt-% of the resin.

17. The article of claim 9 wherein the tackifying resin of the adhesive is a mixture of an aliphatic tackifying resin and an aromatic tackifying resin.

18. The article of claim 1 wherein the adhesive has a Brookfield viscosity of less than 5,000 cps at about 125° C.

19. The article of claim 1 wherein the adhesive has a Brookfield viscosity of less than about 15,000 cps at about 135° C.

20. The article of claim 1 wherein the storage modulus ranges from about $5\times10^4$ dynes/cm$^2$ to about $5\times10^6$ dynes/cm$^2$ at temperatures ranging from about 20° C. to about 60° C.

21. The article of claim 1 wherein the storage modulus ranges from about $1\times10^5$ dynes/cm$^2$ to about $5\times10^6$ dynes/cm$^2$ at temperatures ranging from about 20° C. to about 60° C.

* * * * *